(12) United States Patent
Jupe

(10) Patent No.: US 7,273,855 B2
(45) Date of Patent: Sep. 25, 2007

(54) USE OF PROHIBITIN RNA IN TREATMENT OF CANCER

(75) Inventor: Eldon R. Jupe, Norman, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 6 days.

(21) Appl. No.: 10/190,942

(22) Filed: Jul. 8, 2002

(65) Prior Publication Data

US 2003/0171316 A1 Sep. 11, 2003

Related U.S. Application Data

(63) Continuation of application No. 09/768,125, filed on Jan. 23, 2001, now abandoned, which is a continuation of application No. PCT/US99/16840, filed on Jul. 24, 1999.

(51) Int. Cl.
  A61K 31/70 (2006.01)
  C07H 21/02 (2006.01)
  C07H 21/04 (2006.01)
  C12P 21/63 (2006.01)
  C12N 5/00 (2006.01)
  C12N 15/00 (2006.01)
  C12N 15/63 (2006.01)

(52) U.S. Cl. ............ 514/44; 424/93.1; 424/93.2; 435/320.1; 435/325; 435/455; 536/23.1; 536/23.5

(58) Field of Classification Search ........... 435/69.1, 435/320.1, 325, 455; 536/23.1, 23.5; 424/93.1, 424/93.2; 514/44

See application file for complete search history.

(56) References Cited

U.S. PATENT DOCUMENTS

| 5,658,792 A | 8/1997 | Nuell et al. ............ 435/252.33 |
| 5,776,738 A | 7/1998 | Dell'Orco, Sr. et al. ... 435/91.2 |
| 5,922,852 A | 7/1999 | Dell'Orco, Sr. et al. ... 536/23.1 |

FOREIGN PATENT DOCUMENTS

| WO | WO96/40919 | 12/1996 |
| WO | WO98/20167 | 5/1998 |
| WO | WO99/24614 | 5/1999 |

OTHER PUBLICATIONS

Kelloff et al, Eur. J. Cancer. 35(14):2031-2035, 1999.*
Gomez-Navarro et al, Eur. J. Cancer. 35(6);867-885, 1999.*
Mastrangelo et al, Semin. in Oncology. 23(1): 4-21, 1996.*
Campbell et al, Cancer Epidemiol. Biomarkers Prev.12:1273-1274, 2003.*
Stegmann et al. Biochem. Biophy. Acta. 1325:71-79, 1997.*
PTO-Sequence Search Report for WO 96/40919, conducted 052404.*
PTO-Sequence Search Report for US 5,922,852, conducted 052404.*
New England Biolabs, Catalog 1988-1998, Product # 1230.*
Manjeshwar et al, J. Mol. Hist. 35:639-646, 2004.*
Manjeshwar et al, Cancer Res. 63:5251-5256, 2003.*
Jupe et al., "Prohibitin antiproliferative activity and a lack of heterozygosity in immortalized cell lines," *Exp Cell Res*, 218:577-580, 1995.
Jupe et al., "Prohibitin in breast cancer cell lines: loss of antiproliferative activity is linked to 3' untranslated region mutations," *Cell Growth and Differentiation*, 7:871-878, 1996.
Jupe et al., "The 3' untranslated region of prohibitin and cellular immortalization," *Exp Cell Res*, 224:128-135, 1996.
McClung et al., "Isolation of a cDNA that hybrid selects antiproliferative mRNA from rat liver," *Biochem Bioophys Res Comm*, 164:1316-1322, 1989.
Nagai et al., "Detailed deletion mapping of chromosome segment 17q12-21 in sporadic breast tumors," *Genes, Chromosomes, and Cancer*, 11:58-62, 1994.
Nuell et al., "Prohibitin, an evolutionarily conserved intracellular protein that blocks DNA synthesis in normal fibroblasts and HeLa cells," *Mol Cell Bio*, 11:1372-1381, 1991.
Wang et al., Prohibitin, a potential tumor suppressor, interacts with RB and regulates E2F function, *Oncogene*, 18:3501-3510, 1999.
White et al., "Assignment of the human prohibitin gene (PHB) to Chromosome 17 and identification of a DNA polymorphism," *Genomics*, 11:228-230, 1991.
Jupe et al., The prohibition of 3'UTR as a susceptibility marker and therapeutic in breast cancer, *Proceedings of the American Association for Cancer Research*, 40:481, 1999 (Abstract #3175).

* cited by examiner

*Primary Examiner*—Sumesh Kaushal
(74) *Attorney, Agent, or Firm*—Fulbright & Jaworski, LLP

(57) ABSTRACT

It has now been found that the introduction of single stranded oligonucleotides of DNA or RNA, particularly RNA transcribed from portions of wild type prohibitin 3'UTR, into tumors leads to arrested cell proliferation. Significant reduction in the size of primary tumors has been observed following direct administration of prohibitin 3'UTR RNA. Induction of systemic immunity, as evidenced by the disappearance of metastases as well as the lack of tumor growth in rechallenged animals following prohibitin RNA therapy, has been observed. Thus, wild type RNAs transcribed from portions of a prohibitin 3'UTR, or single stranded DNAs comprised of portions of a prohibitin 3'UTR, or synthetically-made oligonucleotides of the same sequences, can be directly administered as therapeutic agents against tumors.

15 Claims, 11 Drawing Sheets

```
   1 TGTGGAGGTC AGAGTGGAAG CAGGTGTGAG AGGGTCCAGC AGAAGGAAAC
  51 ATGGCTGCCA AAGTGTTTGA GTCCATTGGC AAGTTTGGCC TGGCCTTAGC
 101 TGTTGCAGGA GGCGTGGTGA ACTCTGCCTT ATATAATGTG GATGCTGGGC
 151 ACAGAGCTGT CATCTTTGAC CGATTCCGTG GAGTGCAGGA CATTGTGGTA
 201 GGGGAAGGGA CTCATTTTCT CATCCCGTGG GTACAGAAAC CAATTATCTT
 251 TGACTGCCGT TCTCGACCAC GTAATGTGCC AGTCATCACT GGTAGCAAAG
 301 ATTTACAGAA TGTCAACATC ACACTGCGCA TCCTCTTCCG GCCTGTCGCC
 351 AGCCAGCTTC CTCGCATCTT CACCAGCATC GGAGAGGACT ATGATGAGCG
 401 TGTGCTGCCG TCCATCACAA CTGAGATCCT CAAGTCAGTG GTGGCTCGCT
 451 TTGATGCTGG AGAACTAATC ACCCAGAGAG AGCTGGTCTC CAGGCAGGTG
 501 AGCGACGACC TTACAGAGCG AGCCGCCACC TTTGGGCTCA TCCTGGATGA
 551 CGTGTCCTTG ACACATCTGA CCTTCGGGAA GGAGTTCACA GAAGCGGTGG
 601 AAGCCAAACA GGTGGCTCAG CAGGAAGCAG AGAGGGCCAG ATTTGTGGTG
 651 GAAAAGGCTG AGCAACAGAA AAAGGCGGCC ATCATCTCTG CTGAGGGCGA
 701 CTCCAAGGCA GCTGAGCTGA TTGCCAACTC ACTGGCCACT GCAGGGGATG
 751 GCCTGATCGA GCTGCGCAAG CTGGAAGCTG CAGAGGACAT CGCGTACCAG
 801 CTCTCACGCT CTCGGAACAT CACCTACCTG CCAGCGGGGC AGTCCGTGCT
 851 CCTCCAGCTG CCCCAGTGAG GGCCCACCCT GCCTGCACCT CCGCGGGCTG
 901 ACTGGGCCAC AGCCCCGATG ATTCTTAACA CAGCCTTCCT TCTGCTCCCA
 951 CCCCAGAAAT CACTGTGAAA TTTCATGATT GGCTTAAAGT GAAGGAAATA
1001 AAGGTAAAAT CACTTCAGAT CTCTAATTAG TCTATCAAAT GAAACTCTTT
1051 CATTCTTCTC ACATCCATCT ACTTTTTTAT CCACCTCCCT ACCAAAAATT
1101 GCCAAGTGCC TATGCAAACC AGCTTTAGGT CCCAATTCGG GGCCTGCTGG
1151 AGTTCCGGCC TGGGCACCAG CATTTGGCAG CACGCAGGCG GGGCAGTATG
1201 TGATGGACTG GGGAGCACAG GTGTCTGCCT AGATCCACGT GTGGCCTCCG
1251 TCCTGTCACT GATGGAAGGT TTGCGGATGA GGGCATGTGC GGCTGAACTG
1301 AGAAGGCAGG CCTCCGTCTT CCCAGCGGTT CCTGTGCAGA TGCTGCTGAA
1351 GAGAGGTGCC GGGGAGGGGC AGAGAGGAAG TGGTCTGTCT GTTACCATAA
1401 GTCTGATTCT CTTTAACTGT GTGACCAGCG GAAACAGGTG TGTGTGAACT
1451 GGGCACAGAT TGAAGAATCT GCCCCTGTTG AGGTGGGTGG CCTGACTGT
1501 TGCCCCCCAG GGTCCTAAAA CTTGGATGGA CTTGTATAGT GAGAGAGGAG
1551 GCCTGGACCG AGATGTGAGT CCTGTTGAAG ACTTCCTCTC TACCCCCCAC
1601 CTTGGTCCCT CTCAGATACC CAGTGGAATT CCAACTTGAA GGATTGCATC
1651 CTGCTGGGGC TGAACATGCC TGCCAAAGAC GTGTCCGACC TACGTTCCTG
1701 GCCCCTCGT TCAGAGACTG CCCTTCTCAC GGGCTCTATG CCTGCACTGG
1751 GAAGGAAACA AATGTGTATA AACTGCTGTC AATAAATGAC ACCCAGACCT
1801 TCC
```

Fig. 1

```
  1  CCCAGAAATC ACTGTGAAAT TTCATGATTG GCTTAAAGTG AAGGAAATAA
 51  AGGTAAAATC ACTTCAGATC TCTAATTAGT CTATCAAATG AAACTCTTTC
101  ATTCTTCTCA CATCCATCTA CTTTTTTATC CACCTCCCTA CCAAAAATTG
151  CCAAGTGCCT ATGCAAACCA GCTTAGGTC  CCAATTCGGG GCCTGCTGGA
201  GTTCCGGCCT GGGCACCAGC ATTGGCAGC  ACGCAGGCGG GGCAGTATGT
251  GATGGACTGG GGAGCACAGG TGTCTGCCTA GATCCACGTG TGGCCTCCGT
301  CCTGTCACTG ATGGAAGGTT TGCGGATGAG GCATGTGCG  GCTGAACTGA
351  GAAGGCAGGC CTCCGTCTTC CAGCGGTTC  CTGTGCAGAT GCTGCTGAAG
401  AGAGGTGCCG GGAGGGGCA  GAGAGGAAGT GGTCTGTCTG TTACCATAAG
451  TCTGATTCTC TTTAACTGTG TGACCAGCGG AAACAGGTGT GTGTGAACTG
501  GGCACAGATT GAAGAATCTG CCCCTGTTGA GGTGGGTGGG CCTGACTGTT
551  GCCCCCAGG  GTCCTAAAAC TTGGATGGAC TTGTATAGTG AGAGAGGAGG
601  CCTGGACCGA GATGTGAGTC CTGTTGAAGA CTTCCTCTCT ACCCCCCACC
651  TTGGTCCCTC TCAGATACCC AGTGGAATTC CAACTTGAAG GATTGCATCC
701  TGCTGGGGCT GAACATGCCT GCCAAAGACG TGTCCGACCT ACGTTCCTGG
751  CCCCCTCGTT CAGAGACTGC CCTTCTCACG GGCTCTATGC CTGCACTGGG
801  AAGGAAACAA ATGTGTATAA ACTGCTGTCA ATAAATGACA CCCAGACCTT
851  CC
```

Fig. 2

```
  1  GATAATACGA CTCACTATAG GGTGAGTCCT GTTGAAGACT TCCTCTCTAC
 51  CCCCCACCTT GGTCCCTCTC AGATACCCAG TGGAATTCCA ACTTGAAGGA
101  TTGCATCCTG CTGGGGCTGA ACATGCCTGC CAAAGACGTG TCCGACCTAC
151  GTTCCTGGCC CCCTCGTTCA GAGACTGCCC TTCTCACGGG CTCTATGCCT
201  GCACTGGGAA GGAAACAAAT GTGTATAAAC TGCTGTCAAT AAATGACACC
251  CAGACCTTCC
```

Fig. 3

Alignment of human (top) and rat (bottom) 3' end of the 3'UTR

```
614 ..................................................................GTGAGTCCTGTTGAAG 629
                                                                      ||||||||||| ||||
    ..................................................................GTGAGTCCTGTGGAAG

630 ACTTCCTCTCTACCCCCCACCTTGGTCCCTCTCAGATACCCAGTGGAATT 679
    ||||||| || ||||||||| ||||| ||||||| |||||||| ||| |||
    ACTTCCTGTCCACCCCCCACATTGGT.CCTCTCAAATACCCAATGGGATT

680 CCAACTTGAAGGATTGCATCCTGCTGGGGCTGAACATGCCTGCCAAAGAC 729
    ||| |||||||||||||||||||||||| |||||||| || |||||||| |||
    CCAGCTTGAAGGATTGCATCCTGCCGGGGCTGAGCACACCTGCCAAGGAC

730 GTGTCCGACCTACGTTCCTGGCCCCCTCGTTCAGA...GACTGCCCTTCTC 777
    || || |   | ||   ||| ||| |  ||| | |   ||||| |
    ACGTGCGCCTGCCTTCCCGCTCCCTCTCTTCGAGATTGCCCTTCCTTCCC

778 ACGGGCTCTATGCCTGCACTGGGAAGGAAACAAATGTG............ 815
    |  ||||| | ||| | ||  ||||||| |||     |
    AAGGGCTGTGGGCCAGAGCTCCGAAGGAAGCAATCAAGGAAAGAAAACAC

816 ..TATAAACTGCTGTCAATAAATGACACCCAGACCTTCC            852
      | ||| |||||||||||||||||||||||||||||| ||
    AATGTAAGCTGCTGTCAATAAATGACACCCAGACCCTCA
```

% Identity : 78.151

Fig. 4

```
1548  GACACGTGCGCCTGCCTTCCCGCTCCTCTCTTCGAGATTGCCCTTCCTT  1597
      ||||||||||||||||||||||||||||||||||||||||||||||||
      GACACATGCCTACCTTCCCGCCCCTCTCCGAGATTGCCCTTCCTT

1598  CCCAAGGGCTGTGGGCCAGAGCTCCGAAGGAAGCAATCAAGGAAAGAAAA  1647
      ||||||||||||||||||||||||||||||||||||||||||||||||
      CCCAAGGGCTGTGGGTCACTGCTCCAAAGGAAGCAATCAAGGAAAGAAAA
```

USE OF PROHIBITIN RNA IN TREATMENT OF CANCER

This is a continuation, of prior application Ser. No. 09/768,125, filed Jan. 23, 2001, now abandoned, which is a continuation of PCT/US99/16840 filed 24 Jul. 1999 and designating the U.S.

TECHNICAL FIELD OF INVENTION

This invention relates generally to use of single-stranded oligonucleotides for the treatment of cancer and particularly to the use of a portion of a 3' UTR from a prohibitin gene (DNA) or a transcript thereof (RNA) for inhibiting the growth of cancer cells in animals.

BACKGROUND OF THE INVENTION

Division of normal cells is controlled by complex interactions between factors telling the cell to divide and other factors telling the cell to stop dividing. Controlling the steps of cell division, collectively known as the cell cycle, is a complex interplay between promoter (oncogenes) and suppressor genes.

Cancer is a disease resulting from uncontrolled cell division caused by mutations in promoter (oncogenes) and/or suppressor genes. In cancer cells, oncogene products are over expressed and tumor suppressor gene products are lost. Initial evidence for the existence of tumor suppressor genes emerged from studies of chromosomal deletions in familial cancer syndromes. Deletions in these same regions are also often observed in sporadic cancers. The restoration of a single copy of a missing or altered tumor suppressor gene will often re-establish control over the growth of cancerous cell lines and suppress tumor formation in animal cancer models.

Many genes and their products with positive effects on cell proliferation such as growth factors and their cognate receptors, transcription factors, and cyclins and cyclin dependent kinases have been identified and extensively studied. These represent oncogenes whose aberrant overexpression leads to uncontrolled growth. Genes involved in cell cycle arrest have been more difficult to isolate and characterize because of their recessive nature. These tumor suppressors or negative regulators of cell proliferation exhibit loss of function in tumors.

Tumor suppressor genes code for negative regulators that suppress the proliferation of cells and are of immense interest because of their importance in understanding normal and cancerous cell growth. The prohibitin 3' untranslated region (3' UTR) falls into a major category of tumor suppressors that are inhibitors of DNA synthesis. The cDNA coding for prohibitin was originally identified and cloned in a screen to discover senescence regulating mRNAs highly expressed in normal compared to regenerating rat liver (McClung, et al 1989 "Isolation of a cDNA that hybrid selects antiproliferative mRNA from rat liver," *Biochem Biophys Res Comm* 164.1316-1322; and Nuell, et al 1991 "Prohibitin, an evolutionarily conserved intracellular protein that blocks DNA synthesis in normal fibroblasts and HeLa cells," *Mol Cell Bio* 11.1372-1381).

The human prohibitin gene maps to chromosome 17 at q21 near BRCA1, and two alleles (designated "B" and "non-B") have been described. (Jupe, et al. 1995 "Prohibitin antiproliferative activity and a lack of heterozygosity in immortalized cell lines," *Exp Cell Res* 218.577-580, Jupe et al 1996 "The 3' untranslated region of prohibitin and cellular immortalization," *Exp Cell Res* 224:128-135, Jupe, et al. 1996 "Prohibitin in breast cancer cell lines loss of antiproliferative activity is linked to 3' untranslated region mutations," *Cell Growth and Differentiation* 7:871-878; and White, et al. 1991 "Assignment of the human prohibitin gene (PHB) to chromosome 17 and identification of a DNA polymorphism," *Genomics* 11.228-230). In both human and rat, the prohibitin gene has six introns and seven exons (Altus, et al 1995 "Regions of evolutionary conservation between rat and human prohibitin-encoding genes," *Gene* 158:291-294) and produces two transcripts, one apparently 1.2 and the other 1.9 kb in length, as defined by Northern blotting experiments (Nuell, et al 1991 *Mol Cell Bio* 11 1372-1381, Jupe, et al 1995. *Exp Cell Res* 218.577-580, Jupe et al 1996. *Exp Cell Res* 224.128-135; and Jupe, et al 1996 *Cell Growth and Differentiation* 7 871-878). Both transcripts code for the same 30,000 Dalton protein, and in mammalian tissues, the level of protein expression generally parallels the level of total message (Nuell, et al. 1991. *Mol Cell Bio* 11:1372-1381; Jupe, et al 1995 *Exp Cell Res* 218 577-580, Jupe et al 1996 *Exp Cell Res* 224 128-135, Jupe, et al 1996 *Cell Growth and Differentiation* 7 871-878, White, et al 1991 *Genomics* 11 228-230, Altus, et al 1995 *Gene* 158 291-294, and McClung, et al 1995 "Prohibitin, potential role in senescence, development, and tumor suppression," *Exp Gerontol* 30 99-124). In addition to rat and human, prohibitin has been cloned from mouse (Terashima, et al 1994 "The IgM antigen receptor of B lymphocytesis associated with prohibitin and a prohibitin-related protein," *EMBO J* 13 3782-3792), yeast (Franklin, D. S. and Jazwinski, S M. 1993. "A yeast homolog of the rat prohibitin gene is differentially expressed and determines longevity in *Saccharomyces cerevisiae, J Cell Biochem* Suppl 17D 159), *Drosophila* (Eveleth, D. D J and Marsh, J. L 1986. "Sequence and expression of the Cc gene, a member of the dopa decarboxylase gene cluster of *Drosophila*, possible translational regulation," *Nucleic Acids Res,* 14 6169-6183), and *Pneumocystis carinii* (Narasimhan, et al. 1997. "Prohibitin, a putative negative control element present in *Pneumocystis carinii,"* *Infection and Immunity* 65 5125-5130). The protein is highly conserved throughout evolution, and the deduced amino acid sequences of human and rat prohibitin are identical except for one conservative amino acid change (McClung, et al 1995. *Exp Gerontol* 30.99-124, and Sato, et al. 1992 "The human prohibitin gene located on chromosome 17q21 is mutated in sporadic breast cancer," *Cancer Res* 52 1643-1646). The majority of the protein is localized to the mitochondria, and roles in diverse processes such as cellular aging in yeast (Jazwinski, S. M. 1996 "Longevity, genes, and aging," *Science* 273:54-59, and Coates, et al. 1997. "The prohibitin family of proteins regulate replicative lifespan," *Current Biology* 7:R607-R610), development and viability in *Drosophila* (Eveleth, D. D J. and Marsh, J L 1986 *Nucleic Acids Res,* 14 6169-6183), and granulosa cell proliferation in mammals (Thompson, et al 1997 "Steroidogenic acute regulatory (StAR) protein (p25) and prohibitin (p28) from cultured rat ovarian granulosa cells," *J Reproduct Fertility* 109.337-348) have been reported. In yeast and *Pneumocystis*, prohibitin protein has been shown to have a possible role in the ras signalling pathway (Narasimhan, et al 1997. *Infection and Immunity* 65 5125-5130, and Jazwinski, S M 1996 *Science* 273 54-59). Prohibitin has been shown to interact with retinoblastoma tumor suppressor proteins (Rb) in vivo and in vitro and was effective in repressing E2F-mediated transcription, while a prohibitin mutant could not bind to Rb, repress E2F activity, or inhibit cell proliferation (Wang, et l 1999 "Prohibitin, a potential tumor suppressor, interacts with RB and regulates E2F function," *Oncogene* 18:3501-3510).

Prohibitin gene structure and function have been examined in eleven immortalized human cell lines which have been classified into four complementation groups (A-D) (Jupe, et al. 1995 *Exp Cell Res* 218.577-580; and Jupe et al. 1996. *Exp Cell Res* 224 128-135). Human breast cancer cell lines have also been examined because the gene is located at 17q21, a chromosomal region that frequently undergoes loss of heterozygosity (LOH) in sporadic and familial breast cancers (Nagai, et al 1994 "Detailed deletion mapping of chromosome segment 17q12-21 in sporadic breast tumors," *Genes, Chromosomes, and Cancer* 11:58-62). Cell proliferation assays performed following the introduction of full length (19 kb) wild type prohibitin RNA showed that normal human diploid fibroblasts (HDF), 75% of breast cancer cell lines examined, and all four Group B cell lines (but no cell lines from any of the other groups) were inhibited at the G1-S transition in the cell cycle (Jupe, et al. 1995. *Exp Cell Res* 218.577-580, Jupe et al 1996. *Exp Cell Res* 224.128-135; and Jupe, et al 1996 *Cell Growth and Differentiation* 7 871-878). Surprisingly, sequence analysis of the prohibitin gene showed that the 3' UTR from prohibitin sensitive cancer cell lines differed from wild type at one or more bases, while the 3' UTR from insensitive lines exhibited the wild type sequence. There were no coding region sequence alterations in any of the cell lines. (Jupe, et al 1995. *Exp Cell Res* 218:577-580, Jupe et al. 1996 *Exp Cell Res* 224:128-135; and Jupe, et al. 1996. *Cell Growth and Differentiation* 7.871-878). These findings suggest that the loss of growth control in the cancer cell is due to mutations in the prohibitin 3' UTR.

International Application No. WO 96/40919 published Dec. 19, 1996, disclosed that mutations in the 3' UTR of the B type allele are diagnostic for increased susceptibility to breast cancer and that reintroduction of either a portion or entire normal 3' UTR of the prohibitin gene into early stage tumors can be employed as a therapeutic agent for treatment of cancer.

International Application No. WO 98/20167 published May 14, 1998, disclosed a method for determining a patient's susceptibility to breast cancer by identifying the patient's germline genotype at position 729 in the prohibitin 3' UTR (SEQ ID NO 2) from either genomic DNA or RNA transcribed from genomic DNA which contains the 3' UTR of the prohibitin gene.

International Application No. WO 99/24614 published May 20, 1999, disclosed a method for determining a patient's susceptibility to other types of cancer besides breast cancer (e.g., prostate or ovarian cancer) by identifying the patient's germline genotype at position 729 in the prohibitin 3' UTR (SEQ ID NO:2) from either genomic DNA or RNA transcribed from genomic DNA which contains the 3' UTR of the prohibitin gene.

U.S. Pat. No. 5,776,738 issued Jul. 7, 1998 and U.S. Pat. No. 5,922,852 issued Jul. 13, 1999 disclosed a purified nucleic acid fragment consisting of a portion of the 3' UTR region of the prohibitin gene which can be used in determining a patient's susceptibility to breast cancer and other cancers.

It has now been found that the introduction of single stranded oligonucleotides, preferably DNA from the 3' UTR of wild-type prohibitin or RNA transcribed therefrom, or synthetically manufactured oligonucleotides of like sequence, most preferably RNA transcribed from the wild type prohibitin 3' UTR, into three breast cancer cell lines leads to arrested cell proliferation, while RNA transcribed from mutated prohibitin 3' UTR has no antiproliferative activity. Thus, growth control is reestablished when wild-type prohibitin RNA is introduced. Whereas cellular proliferation assays have previously demonstrated cell cycle arrests following the introduction of genes coding for p53 or p21 cyclin dependent kinase inhibitor (i.e., WAF1, SD11, CAP20 or CIP1) and subsequent production of functional protein, it has now been found that wild type RNAs transcribed from portions of the prohibitin 3' UTR (or other oligonucleotides as described herein) can be directly administered as therapeutic agents against cancer, thus bypassing the requirements of the more "traditional" gene therapy approaches where a protein-producing gene is introduced into the cell or chromosome.

SUMMARY OF THE INVENTION

The present invention comprises oligonucleotides derived from the sequences of a 3' untranslated region (3' UTR) of a prohibitin gene. In one aspect, the invention comprises an isolated ribonucleic acid transcribed from a portion of the 3' untranslated region of the prohibitin gene which has tumor suppressor activity in animals, preferably mammals. A preferred ribonucleic acid is a transcript of the entire 3' untranslated region of the prohibitin gene, depicted in SEQ ID NO.1 from position 867 to 1803. More preferred, the ribonucleic acid is a transcript from position 952 to 1803 of SEQ ID NO.1, also shown as SEQ ID NO 2. Another preferred ribonucleic acid is a transcript from position 1566 to 1803 of SEQ ID NO.1, the final 238 nucleotides of the 3' end of the 3' untranslated region of the prohibitin gene. SEQ ID NO 3 depicts this preferred sequence preceded by a T7 promotor.

Single stranded DNA derived from the 3' UTR which mimics the three dimensional conformation of the RNA described above also comprise oligonucleotides of the present invention. Preferably, it is comprised of bases from position 867-1 803 of SEQ ID NO.1, 952 to 1803 of SEQ ID NO.1, and most preferably 1566-1803 of SEQ ID NO:1.

The present invention also includes DNA from which the RNA transcripts are transcribed. In addition, the RNA and DNA can be made synthetically through methods known in the art by using the sequence information provided herein.

In another aspect, the present invention is a pharmaceutical preparation adapted for administration to obtain an anticancer effect, comprising a proliferation-inhibiting amount of active isolated oligonucleotides. In one aspect, an isolated ribonucleic acid from a portion of the 3' untranslated region of the prohibitin gene can be used in a pharmaceutical preparation. The preparation may include any of the RNAs or DNAs described above. The pharmaceutical preparation comprising a ribonucleic acid can be administered so that it directly contacts a tumor. The preferred method is by intra-tumoral injection. The dosage amount for directly contacting a tumor is at from about 2 micrograms to about 120 micrograms per cubic centimeter of tumor. The volume of the tumor can be estimated by ultrasonic visualization or other methods for estimation known in the art of medicine. The pharmaceutical preparation can also be administered systemically. The dosage amount for systemic administration by continuous infusion (iv) is at from about 0.5 milligrams to about 200 milligrams per kilogram body weight per day for one to fifteen days. More preferably the dosage is from 1-100 mg/kg/day.

In another aspect, single stranded DNA oligonucleotides as described above may be used.

In yet another aspect, the present invention is a method of inhibiting the proliferation of cancer cells comprising contacting cancer cells with a proliferation-inhibiting amount of an active isolated oligonucleotide. In one aspect, an isolated ribonucleic acid transcript from a portion of the 3' untranslated region of the prohibitin gene can be used for tumor suppression in animals. The method may include use of any of the RNAs or DNAs described above.

BRIEF DESCRIPTION OF THE DRAWINGS

FIG. 1 (SEQ ID NO 1) shows the sequence (5'→3') of the sense strand of a human prohibitin cDNA of 1803 bases encoding the RNA referred to as the 1.9 kb transcript detected by Northern blotting experiments. The protein coding region of the transcript ends at position 866. The transcript historically referred to as 1.2 kb ends at position 1026. Thus, the sequence from position 1027 to 1803 is 3' UTR that is unique to the longer transcript. An 852 base transcript that overlaps by about 75 bases with the 3' UTR of the 1.2 kb transcript, begins at position 952 and ends at position 1803 of the 1.9 kb transcript (SEQ ID NO.1). This was the first 3' UTR specific fragment shown to have antiproliferative activity (FIG. 2). The antiproliferative activity has now been further localized to the final 238 bases of the 3' UTR (FIG. 3, SEQ ID NO:3). This subfragment represents a portion of the 3' UTR unique to the longer transcript.

FIG. 2 depicts the DNA sequence of the sense strand (5'→3') of the region coding for the 852 base transcript of wild type prohibitin 3' UTR (SEQ. ID NO.2).

FIG. 3 depicts the DNA sequence of the sense strand (5'→3') of the region coding for a 233 base transcript (3' end of 1.9 kb wild type prohibitin 3' UTR) (SEQ ID NO 3). The T7 primer sequence used to produce the RNA from PCR products is underlined at the 5' end. Transcription of the RNA from the T7 promoter contained on a PCR product begins at the first G of the GGG at the end of the promoter. This produces an RNA with 238 bases of prohibitin sequence and two additional Gs on the 5' end.

FIG. 4 depicts the alignment of the 3' end of the 3' UTR of the wild type human (top) and rat (SEQ ID NO:4) (bottom) prohibitin genes, showing 78% identity as determined by the GAP program in the University of Wisconsin GCG package.

FIG. 9 depicts sequence alignment of a portion of the wild type and mutated DNA sequences coding for rat prohibitin 3' UTR (SEQ ID NO: 6, SEQ ID NO: 7). The wild type rat sequence (top) has been previously published, (Nuell, et al 1991. *Mol Cell Biol* 11.1372-1381), while the mutated molecule was cloned from 7,12-dimethylbenz(a)anthracene (DMBA)-induced rat mammary tumor tissue. There are nine mutations over this 100 base region.

DETAILED DESCRIPTION

Figure 5:
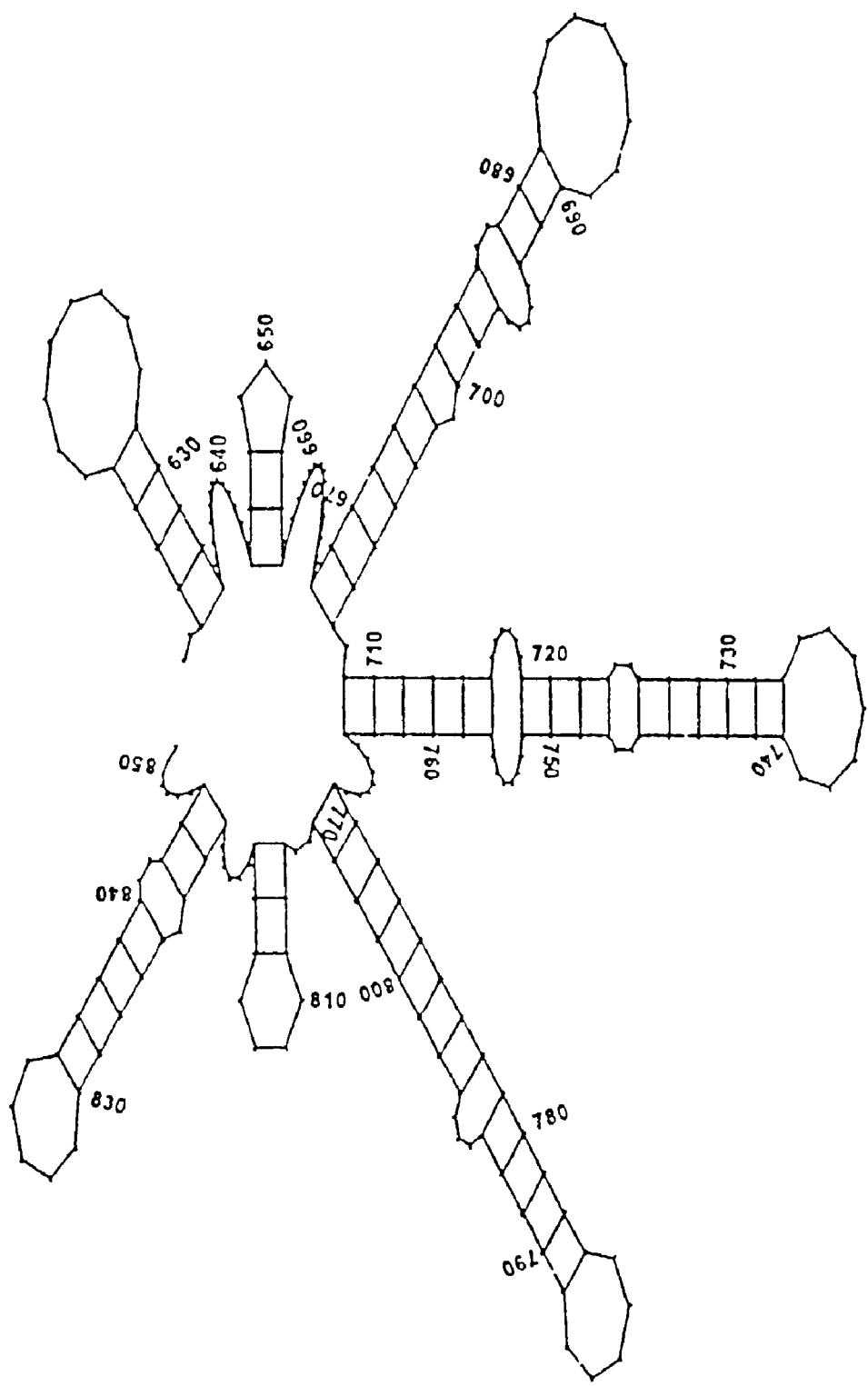
FIG. 5 depicts the predicted secondary structure formed by the wild type therapeutic RNA. The model was generated by the MFOLD program and the graphic representation was generated with the PLOTFOLD program. Both programs were run using the University of Wisconsin GCG package.

Novel oligonucleotides derived from the 3' untranslated region (3' UTR) of the prohibitin gene can be used to reduce proliferation of cancer cells, regress tumors, and treat cancer. For example, RNAs derived from the non-coding prohibitin 3' UTR or single-stranded sense DNAs of the non-coding prohibitin 3' UTR which mimic the three-dimensional conformation of the RNA derived from the non-coding wild type prohibitin 3' UTR can be applied to cells or tumors or administered to patients in need of treatment in order to provide these aforementioned benefits. More specifically, the novel oligonucleotides are preferably derived from the human non-coding 3' UTR of the wild type prohibitin 1.9 kb transcript (FIG. 1 and SEQ ID NO:1). In the 1.9 kb transcript, the protein coding region ends at base number 866. The 1.9 kb transcript contains about 777 bases of unique 3' UTR beginning at position 1027 (FIG. 1 and SEQ ID NO.1) (Jupe et al 1996. *Exp Cell Res* 224:128-135).

The oligonucleotides of the present invention also include animal variants for the treatment of cancer in humans and other animals. For example, oligonucleotides derived from the 3' UTR of the prohibitin gene from a non-human animal which have 50% or greater homology or more preferably 70% or greater homology with the 3' UTR of the human prohibitin gene can be used in the treatment of cancer in humans and other animals. More specifically, as illustrated in the alignment of the wild type human and 3' end of the prohibitin 3' UTR given in FIG. 4, the 3' end of the 3' UTR of the rat prohibitin gene has 78% homology with the 3' end of the 3' UTR of the human prohibitin gene, and, therefore, oligonucleotides comprising the 3' end of the rat 3' UTR can be used to treat cancer in humans and other animals. Experimentally the homology can be defined by hybridization of the human sequence in a salt solution to other animal DNAs (or RNAs) bound to a nylon membrane. The stringency of the reaction is determined by the melting temperature $T_m$ being defined by the formula $T_m$=81 5+0 41(G+C)+ 16 6log [Na$^+$]-0.63(% formamide)-[300+2000 [Na$^+$]-d] where G+C is the % guanosine and cytosine in the probe of known sequence, [Na$^+$] is the molarity of Na$^+$ or equivalent monovalent action and d is the length of the hybridized duplex in nucleotides. Conditions of 40-50° below $T_m$ can be used for very distant homologs. Screening at 30-35° below $T_m$ is usually preferred to identify more closely related homologs.

Oligonucleotide Therapy

The data shown below demonstrate that a short fragment of a prohibitin 3' UTR RNA transcript functions as a regulatory RNA with tumor suppressor activity and is able to effectively control breast tumor cellular proliferation in vivo when administered as a therapeutic. These results indicate the effectiveness of a direct prohibitin 3' UTR RNA therapy for breast cancer in humans and other animals. The presence of mutations in the prohibitin 3' UTR have also been found in other types of cancer and wild type prohibitin RNA can inhibit cell cycle progression in cell lives derived from other types of tumors. Accordingly, direct prohibitin 3' UTR oligonucleotide therapy can also be used in the treatment of other types of cancer.

Prohibitin 3' UTR-derived oligonucleotides can be administered either directly into solid tumors or systemically. If administered prior to the surgical removal of the tumor, shrinkage of the tumor may be sufficient so that surgery is no longer necessary thereby avoiding the possible undesirable release of tumor cells into the circulation as a complication of surgery. The preferred initial dose for oligonucleotides injected directly into a solid tumor in the treatment of cancer is from about 2 micrograms to about 120 micrograms per cubic centimeter tumor, or for systemic treatment 0.5 mg/kg/day to 200 mg/kg/day for one to fourteen days. The more preferred dose for oligonucleotides administered systemically in treatment of cancer is from about 1 to about 100 milligrams per kilogram body weight/day. The treatment can be repeated as deemed desirable.

The oligonucleotides of the present invention can be administered by any means which transmit a proliferation-inhibiting amount of the oligonucleotide into malignant cells. Other methods of administration include direct delivery to the liver via the hepatic portal system, to the nervous system by intra-thecal injection and to the lungs by inhalation. The carrier used can be isotonic saline or more preferably, cationic or anionic liposomes. An alternative method is to insert the oligonucleotide preparation into tissue surrounding the tumor, at which time the oligonucleotides migrate into the malignant cells. The oligonucleotide preparation can be injected by syringe directly into accessible tumors or tissue surrounding accessible tumors, either intraveneously, intramuscularly, intraperitoneally, subcutaneously, or topically. Administration to mucosal surfaces by way of creams, sprays, liquids and swabs is also anticipated. The composition can be administered to the lungs by means of a pulmonary inhaler. Oral administration may also be used.

Prohibitin 3' UTR-derived oligonucleotides are systemically delivered either intraveneously, intramuscularly, intraperitoneally, or subcutaneously; however, other methods known in the art are within the scope of the present invention. The composition may be encapsulated or incorporated into a vehicle used in the pharmaceutical art for delivery such as, for example, liposomes.

In addition, for either direct or systemic treatment, the oligonucleotides can be administered in an expression vector. Expression vectors suitable for oligonucleotides of the present invention include viral vectors, plasmid vectors, and other vehicles known in the art that have been manipulated by insertion of sequences encoding the prohibitin 3' UTR. Preferable expression vectors include eukaryotic viral vectors, for example, bovine papilloma virus, adenovirus, and adeno-associated virus. The expression vector contains a promoter that facilitates the efficient, preferably constitutive, production of the oligonucleotides of interest in the patient. Most preferred for constitutive activity is the cytomegalo virus (CMV) promoter. Promoters specific for the targeted malignant cell type are advantageous, i.e., mammary tumor virus promoter for treatment of breast cancer. Preferable promoters specific for breast tissue include those for milk proteins, e.g. β-casein, β-lactoglobin, or whey acidic proteins.

Alternatively, the oligonucleotide can be combined with a pharmaceutically acceptable carrier or excipient which is selected based on the method of administration. Excipients can include fillers, extenders, binders, disintegrants, surface-active agents, or lubricants for use in a variety of dosage forms including suspensions, emulsions, solutions, creams, gels, salves, and liquid preparations for injection. Tablets, powders, granules, and capsules can be used for oral administration. Various carriers can be used for the delivery of the prohibitin 3' UTR-derived oligonucleotides. Exemplary carriers include saline, the cationic liposome, (N-[1-(2,3-dioleoyloxy)propyl]-N,N,N-tri-methylammonium methylsulfate) (DOTAP, Boehringer Mannheim, Indianapolis, Ind.), and other cationic or anionic liposomes.

Moreover, the success of the direct injection of the prohibitin R-NA into tumors indicated that the structure of the RNA has some inherent stability and nuclease resistance, possibly due to its propensity to form secondary structure (FIG. 5). Migration of the prohibitin RNA on native gels was consistent with the molecule being essentially double-stranded. In addition, modifications to the oligonucleotides of the present invention which improve nuclease resistance and molecular stability can be used in cancer treatment. For example, the addition of a 5' terminal 7-methyl guanosine cap or a poly-A tail confers greater stability to RNA.

The methods for making the prohibitin 3' UTR RNAs of the present invention and methods of treatment with the RNAs are described below. Although the present invention has been presented herein with respect to certain descriptions and examples, one of ordinary skill in the art will appreciate that certain modifications can be made to the present invention without departing from its true spirit and scope.

Localization of Antiproliferative Activity

Localization of the antiproliferative activity into a subfragment of the prohibitin 3' UTR was first performed according to the microinjection assay procedure given in Example 4. The full-length 1.9-kilobase (kb) cDNA of the prohibitin 3' UTR and several truncated cDNAs cloned into either pBSIISK+ (Stratagene, La Jolla, Calif.) or pCRII (Invitrogen, San Diego, Calif.) were used to synthesize RNA transcripts in vitro using the mMESSAGE mMACHINE (Ambion, Inc., Austin, Tex.). Truncated transcripts were synthesized in both the sense and antisense orientation from a clone missing translational signals as well as the AUG start site and the region coding for the first 40 amino acids of the prohibitin protein. The 852 base 3' UTR transcripts beginning approximately 80 bases downstream from the UGA stop codon were synthesized from a 3' UTR clone with wild-type sequence. Transcripts were also synthesized from the first 238 bases of the 852 fragment of the 3' UTR and from the final 238 bases of the 3' UTR.

Figure 6:
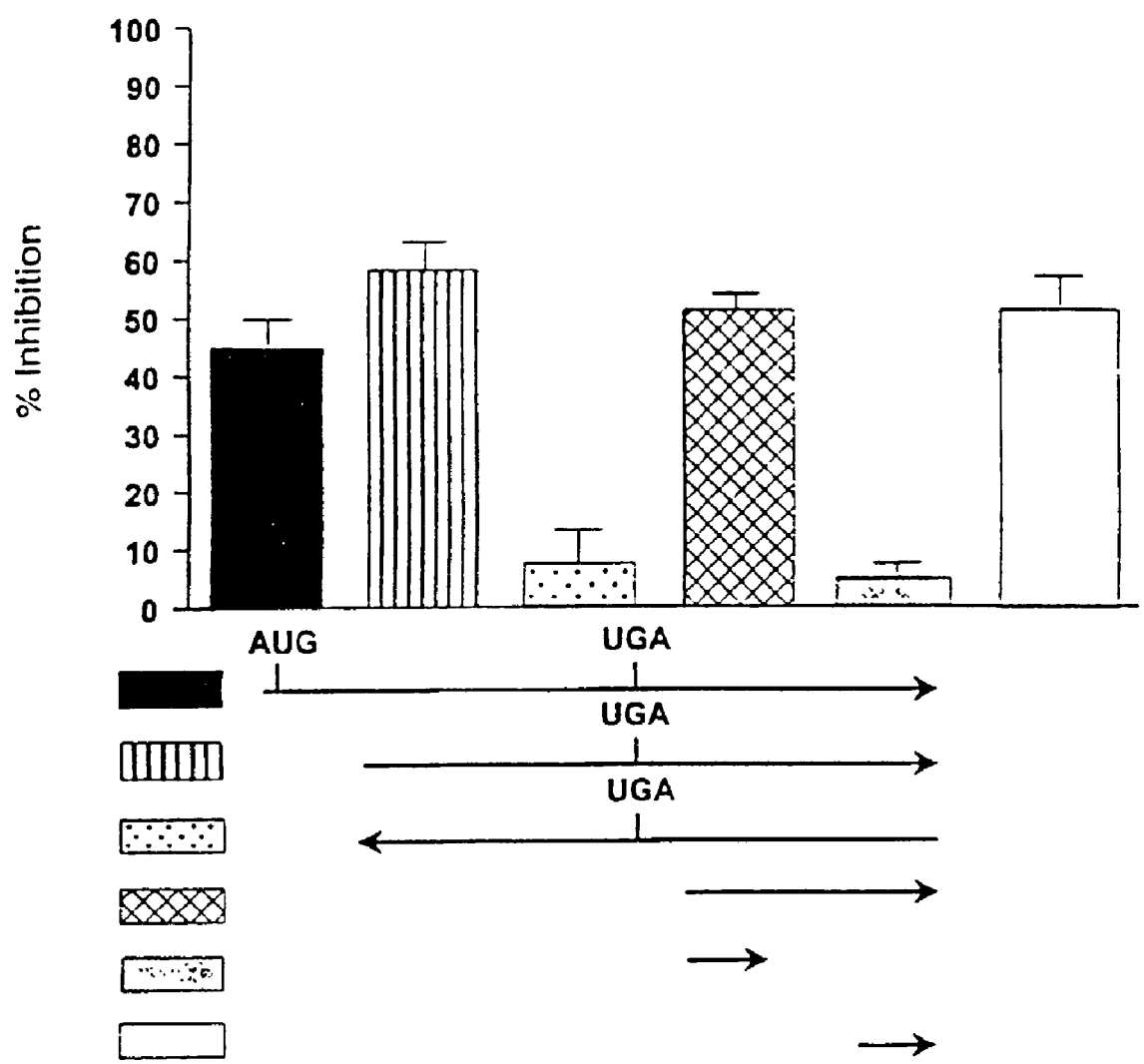
FIG. 6 depicts localization of the antiproliferative activity of prohibitin RNA into a subfragment of the 3' UTR. Schematics of the transcripts used to map the activity to the 3' end of the 3' UTR are shown at the bottom of the figure and coded as closed bar=full length, 1.9 kb (FIG. 1); stripe bar=truncated transcript, missing the start site as well as the codons for the first 40 amino acids of prohibitin protein, dotted bar=antisense of the truncated transcript; cross hatched bar=the 852 base 3' UTR specific transcript (FIG. 2); partially shaded (gray) bar=the first 238 bases of the 852 base 3' UTR; open bar=the last 238 bases from the 3' end of the 3' UTR (FIG. 3). The location of the start (AUG) and termination (UGA) codons are shown. The values reported are the mean inhibition of the percentage of cells in the S phase of the cell cycle calculated from three separate experiments±SEM. Normal HDFs were micro-injected with the indicated RNAs in all of the experiments.

The antiproliferative activity was localized in the wild type prohibitin transcript by comparing the ability of full length and truncated transcripts to inhibit cell cycle progression when microinjected into normal HDFs (FIG. 6). A full length sense transcript truncated at the 5' end, the 852 base non-coding 3' UTR alone (FIG. 2 and SEQ ID NO:2), and the final 238 bases of the 3' UTR (FIG. 3 and SEQ ID NO.3) all exhibited antiproliferative activity comparable to that of the full length 1.9 kb transcript. The truncated antisense transcript and the 238 bases from the 5' end of the 852 base 3' UTR both had little or no antiproliferative activity. Thus, the antiproliferative activity mapped to the final 238 bases of the 3' UTR, indicating that mutation in this region leads to loss of antiproliferative activity.

Figure 7:
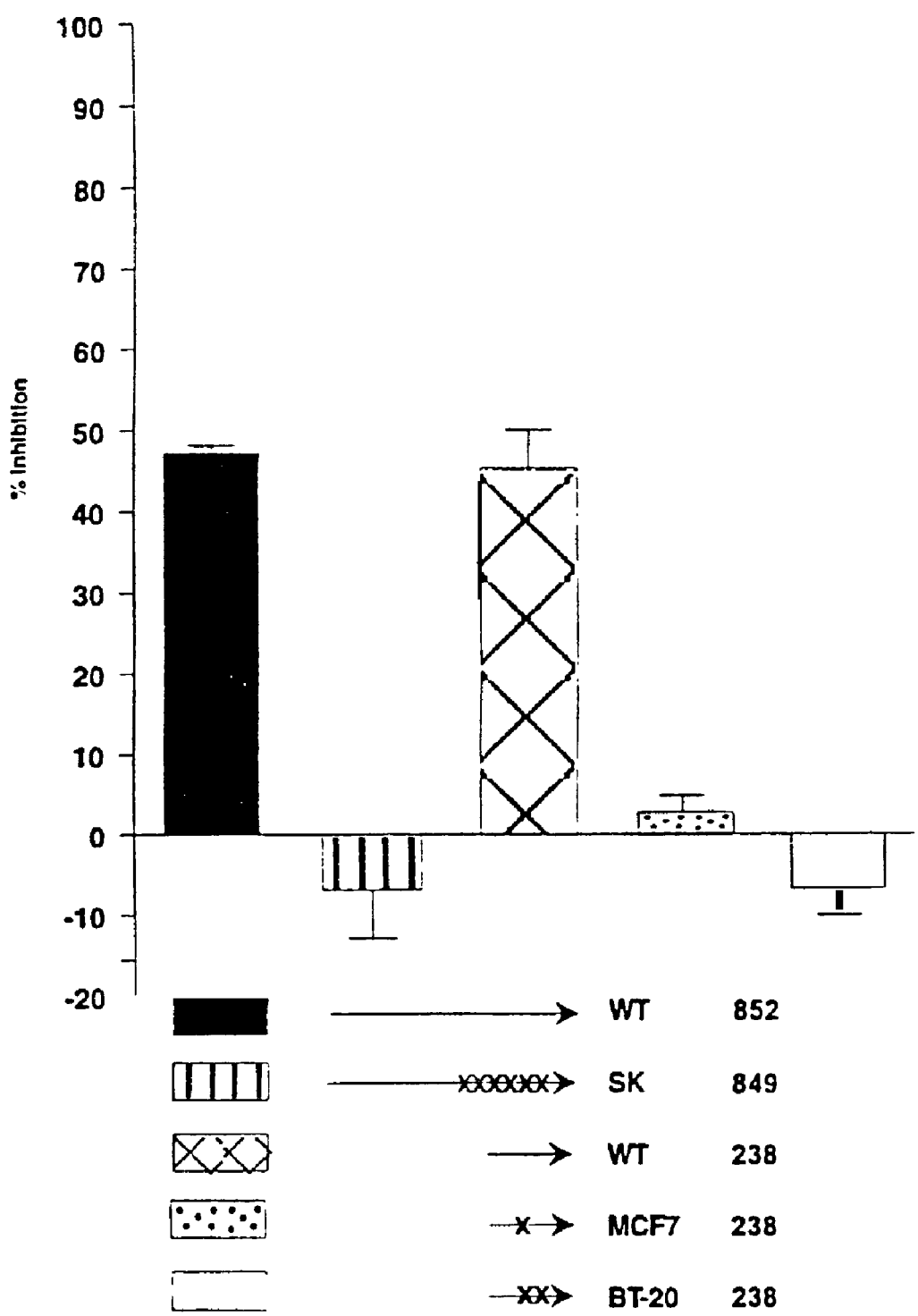
FIG. 7 depicts the effect on cell cycle progression by microinjection of mutated prohibitin 3' UTR transcripts into normal HDFs. Schematics of the 3' UTR transcripts used in each experiment are shown at the bottom of the figure and are coded as closed bar=wild type, 852 base transcript, vertical stripe bar=SK-BR-3 heavily mutated, 849 base transcript, cross-hatched bar=the 3' end of the wild type 3' UTR transcript, 238 base transcript, dotted bar=the 3' end of the MCF7 3' UTR transcript, 238 base transcript; open bar=the 3' end of the BT-20 3' UTR transcript, 238 base transcript. The "x" designations indicate the approximate locations of the mutations. The values reported are the mean inhibition of the percentage of cells in the S phase of the cell cycle calculated from three separate experiments±SEM. Normal HDFs were micro-injected with the indicated RNAs in all of the experiments. The bars with a negative value represent a slight stimulation of cell proliferation.
Figure 8:
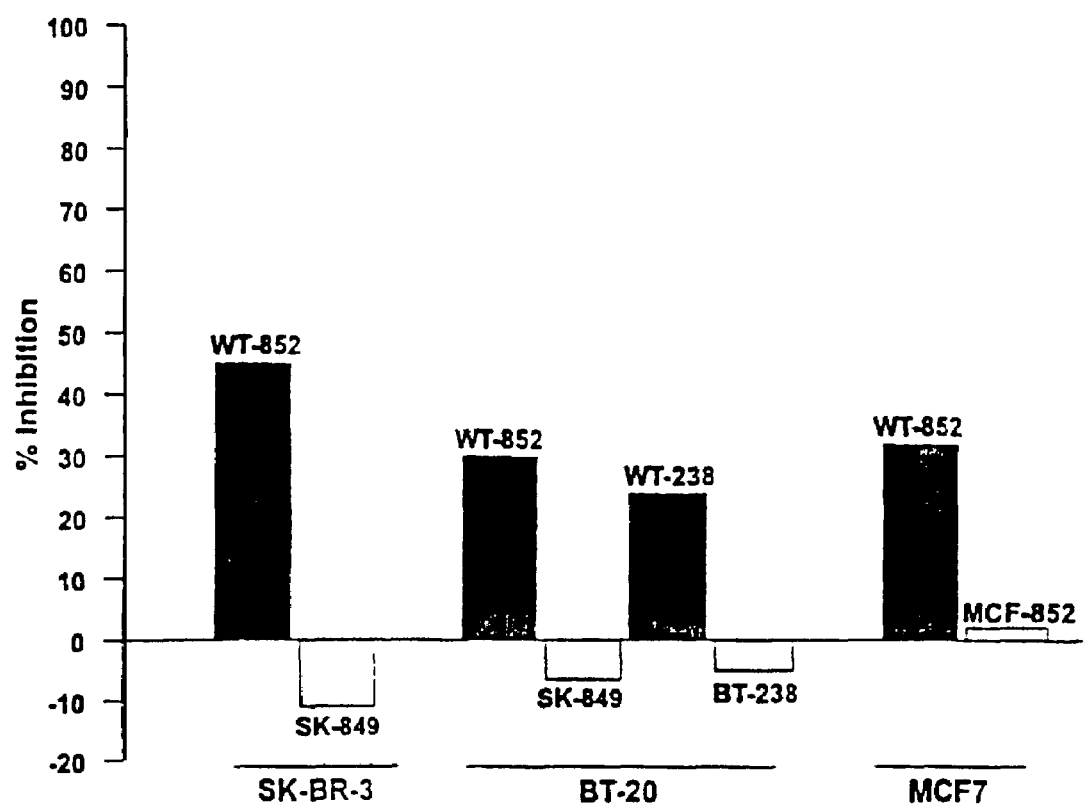
FIG. 8 depicts the effect on cell cycle progression by microinjection of wild type and mutated 3' UTR transcripts into breast cancer cell lines. Wild type (solid bar) or mutated (open bar) transcripts were microinjected into different breast cancer cell lines (shown at bottom of figure). Each bar shows the level of inhibition of the percentage of cells in the S phase of the cell cycle observed for one experiment (200-400 cells tested) and is labeled with the microinjected transcript. The bars with a negative value represent a slight stimulation of cell proliferation.

Antiproliferative Activity of Mutated Prohibitin Transcripts in HDFs and Breast Cancer Cell Lines Antiproliferative activity of prohibitin RNA corresponding to those isolated from three breast cancer cell lines (BT-20, MCF7, and SK-BR-3) was performed according to the microinjection assay procedure given in Example 4. The RNA transcripts were produced according to the method given in Jupe, et al. 1996. *Exp Cell Res*, 224:128-135. The mutated RNAs corresponding to those from three breast cancer cell lines (Table I) were unable to inhibit cell cycle progression in normal HDF (FIG. 7). Even the single cytosine (C-729) to thymine (T-729) transition at UTR-729 which represents an allelic polymorphism was sufficient to eliminate activity from the final 238 bases of the 3' UTR in MCF7. However, BT-20, which is mutated at two other sites but has C-729, also lacked antiproliferative activity, demonstrating that multiple alterations can cause a loss of the 3' UTR's antiproliferative activity. Another experiment illustrated in FIG. 8 showed that in breast cancer cell lines with mutations in the final 238 bases, the wild type 852 and final 238 base RNAs both had antiproliferative activity while mutated ones were inactive, just as they were in HDF. These data show that the antiproliferative activity is localized to the 3' end of the 3' UTR, the most frequently mutated region in breast cancer cell lines (Jupe, et al. 1996 *Cell Growth and Differentiation* 7:871-878) and breast tumors.

Antiproliferative Activity of Prohibitin 3' UTR RNA in Animal Models

RNA prepared by in vitro transcription of a 238 base fragment of the prohibitin 3' UTR (FIG. 3 and SEQ ID NO.3) has been used to treat rat mammary tumors. The RNA was administered by direct injection into a recently emerged palpable tumor. The initial experiments were done with the RNA resuspended in isotonic saline for administration. Using this delivery method, tumors have been completely cured on 50% of treated animals. Modification of the therapeutic RNA by addition of a 5'-terminal-7 methyl guanosine cap, known to stabilize eukaryotic RNA, along with delivery of the RNA complexed with the cationic-liposome DOTAP (N-[1-(2,3-dioleoyloxy)propyl]-N,N,N-tri-methylammonium methylsulfate) led to improved cure rates. The long term survival rate under these conditions was increased to 75%. The successfully treated animals underwent regression of both the treated primary tumor as well as untreated distant metastases.

TABLE I

Prohibitin 3' UTR Mutations in Three Breast Cancer Cell Lines*

| Cell Line | Positions of Base Changes | Base Changes |
| --- | --- | --- |
| BT-20 | 758 | G to A |
|  | 814 | T to C |
| MCF7 | 236 | G to A |
|  | 729 | C to T |
| SK-BR-3 | 691 | G to T |
|  | 696 | C to A |
|  | 702 | G to T |
|  | 711 | G to A |
|  | 729 | C to T |
|  | 734 | C to A |
|  | 736 | G to A |
|  | 737 | A to T |
|  | 741 | A to C |
|  | 742 | C to T |
|  | 752 | C to T |
|  | 753 | C to T |
|  | 757 | C to T |
|  | 771 | C to T |
|  | 778 | A to C |
|  | 779 | C to A |
|  | 787 | A to G |
|  | 794 | C to T |
|  | 795 | A to G |
|  | 798 | G to T |
|  | 799 | G to T |
|  | 802 | ΔA |
|  | 803 | ΔG |
|  | 804 | ΔG |
|  | 808 | C to T |
|  | 810 | A to G |
|  | 813 | G to C |
|  | 825 | C to T |
|  | 829 | C to T |

*The prohibitin sequence of breast cancer cell lines was compared to the wild type sequence from normal HDFs (GenBank Acc. #U49725). Two base changes are present in BT-20 and MCF7, but 26 base changes and a 3 base deletion at 802-804 are detected in SK-BR-3.

RNA Production. Prohibitin RNA was prepared by in vitro transcription using either the mMESSAGE mMACHINE™ or the MEGAScript™ transcription kit (Ambion). The mMESSAGE mMACHINE includes a cap analog (m$^7$G (5')ppp(5')G) in the reaction which incorporates a 5' terminal G into the transcript. This 7-methyl guanosine cap structure at the 5' end of the eukaryotic RNAs confers greater stability to the molecule. Transcription templates used were either a cloned and sequenced plasmid containing the wild type human (or rat) prohibitin 3' UTR or a PCR product subfragment synthesized from the cloned plasmid using prohibitin primers with minimal phage promoters (T7 or SP6) attached (transcription-linked primers) (FIG. 3, SEQ ID NO.3). Following transcription, an aliquot of the reaction was assayed on denaturing agarose gels to confirm the integrity and estimate the yield of full length transcripts. The in vitro transcripts were digested with RNase-free DNaseI. The RNA was then purified on 1.5% agarose gels, eluted from the gel, ethanol precipitated and resuspended in RNase-free water. Alternatively, after DNaseI digestion, the reaction was stopped by adding nuclease-free water and ammonium acetate. The mixture was then phenol/chloroform extracted, chloroform extracted and precipitated with isopropyl alcohol. The precipitated samples were resuspended in sterile, RNase free water. The concentration of RNA was determined spectrophotometrically.

Formulation in Isotonic Saline. The amount of RNA required to achieve the desired dose was reprecipitated using ammonium acetate and isopropanol and resuspended at a concentration of 0.5-1.0 microgram/microliter (μg/μl) in pyrogen-free isotonic saline (Baxter Healthcare Corp., Deerfield, Ill., 0.9% sodium chloride) for administration. RNA for injection was prepared by further diluting 10 to 100 micrograms to a final volume of 100-200 microliters of isotonic saline.

Formulation in DOTAP. The preferred method of RNA delivery involves the formation of a complex with N-[1-(2,3-Dioleoyloxy)propyl]-N,N,N,-trimethylammonium methylsulfate (DOTAP; Roche Molecular Biochemicals, Indianapolis, Ind.), a reagent commonly used for cationic liposome-mediated transfection of eukaryotic cells. The RNA/DOTAP complexes were formed in a HEPES-buffered saline (HBS) (1× HBS=20 mM HEPES, 150 mM NaCl, pH 7 4) following the general guidelines provided in the manufacturer's instructions. The mixture for injection was prepared as follows for a 200 microliter delivery volume containing a dose of 20 micrograms of RNA. A 100 microliter DOTAP solution was prepared by adding 30 microliters of DOTAP stock (1 microgram/microliter) to 70 microliters of 1×HBS. A 100 microliter solution of RNA stock was prepared by adding 20 micrograms of RNA (typically 20 microliters) and 10 microliters of 10×HBS to 70 microliters of RNAase free water. The nucleic acid solution was transferred dropwise into the DOTAP solution and mixed by pipetting 5-10 times. The RNA/DOTAP mixture was incubated for at least 10 minutes at room temperature prior to injection.

Treatment. The RNA prepared for delivery in either isotonic saline or as a DOTAP complex was directly injected into palpable tumors using a 28 gauge, 1 cc insulin syringe. In the rat mammary tumors, 100-200 microliters of solution were typically delivered. Tumor radius was determined by measuring the diameter at the point of greatest length ($D_1$) and width ($D_2$) with calipers and dividing by 2 to calculate radius $R_1$ and $R_2$ respectively. The volume in cubic centimeters is calculated by the formula $4/3\ \pi R_1^2 R_2$ where $R_1 \leq R_2$. Volume of internal tumors may be estimated by ultrasound or X-ray techniques.

Production of Single-Stranded DNA. One method of producing single-stranded DNA of a chosen strand is a modification of the polymerase chain reaction (PCR) in which unequal concentrations of the two amplification primers are used (asymmetric PCR). The single stranded DNA produced by this method can be purified on native or denaturing gels. The single stranded DNA band is excised and prepared for use by organic extraction and ethanol precipitation, as described above for RNA. See, e.g., Peter McCabe (1990) Production of Single-Stranded DNA by Asymmetric PCR. In: M. A. Innis, D. H. Gelfand, J. J. Sninsky, T. J. White,eds. PCR Protocols: A Guide to Methods and Applications. Academic Press San Diego, pp 76-91. The sequences are selected from those which would be appropriate for transcription to RNA, as described above, but since DNA can be used as the therapeutic agent, no transcription is required. Rather, the single-stranded DNA prepared is utilized instead of RNA transcripts in the methods for treatment described herein.

Synthesized Oligonucleotides

DNA or RNA oligonucleotides can be made synthetically, i.e. by use of automatic chemical synthesis or other methods known or which become available in the art. The sequences for synthesis are selected from those described for transcripted RNA or DNA derived from a 3'UTR of a prohibitin gene.

EXAMPLE 1

The efficacy of prohibitin 3' UTR RNA therapy was determined by direct injection into palpable 7,12-dimethylbenz(a)anthracene (DMBA)-induced mammary tumors in rats. These are aggressively growing transplantable, metastatic mammary tumors that overexpress p53 and are propagated in female Wistar-Furth rats. This rat mammary tumor was originally induced in a female Wistar-Furth rat after exposure to 40 mg of DMBA (Kollmorgen, et al. 1983 "Influence of dietary fat and indomethacin on the growth of transplantable mammary tumors in rats," *Cancer Res* 43 4714-4719, and Kim, U 1980 "Characteristics of metastasizing and non-metastasizing tumors and their interaction with the host immune system in the development of metastasis" In Hellman, K., Hilgar, P., and Eccles, S. (eds), *EORTC Metastasis Group International Conference on Clinical and Experimental Aspects of Metastasis*, The Hague Martinus Nijhoff Publisher, pp. 210-214 ). The tumor was maintained by passage every 30 days in 21 day old female, Wistar-Furth rats (130-140 grams). Primary tumor was homogenized to a single cell suspension in Dulbecco's Modified Eagle's Medium (DMEM) with 50 μg/ml gentamycin and 7% newborn calf serum ($1 \times 10^7$ cells/ml). Each animal received $1 \times 10^6$ cells delivered in 200 microliters, injected into the fat pad of the sixth mammary gland, which is adjacent to the right inguinal lymph node. Palpable primary tumors at the injection site were evident between Day 10-12, and metastases were found in lymph nodes, lung, and liver by 20-30 days post injection. It was found for the first time that the tumor overexpressed p53 and had a mutated prohibitin 3' UTR (FIG. 9).

The 238 base RNA from the 3' end of the prohibitin 3' UTR was prepared by in vitro transcription with T7 polymerase using the MEGASCRIPT™ Transcription kit (Ambion) from a cloned and sequenced plasmid. After transcription, an aliquot of the reaction was assayed on denaturing agarose gels to confirm the production of full length transcripts. The in vitro transcripts were treated twice with RNase-free DNase. The RNA was then purified on 1.5% agarose gels, eluted from the gel slice, ethanol precipitated and resuspended in RNase-free water. The concentration was determined spectrophotometrically, and samples reprecipitated and resuspended in sterile, pyrogen-free isotonic saline (Baxter Healthcare Corp.) for administration.

Figure 10:
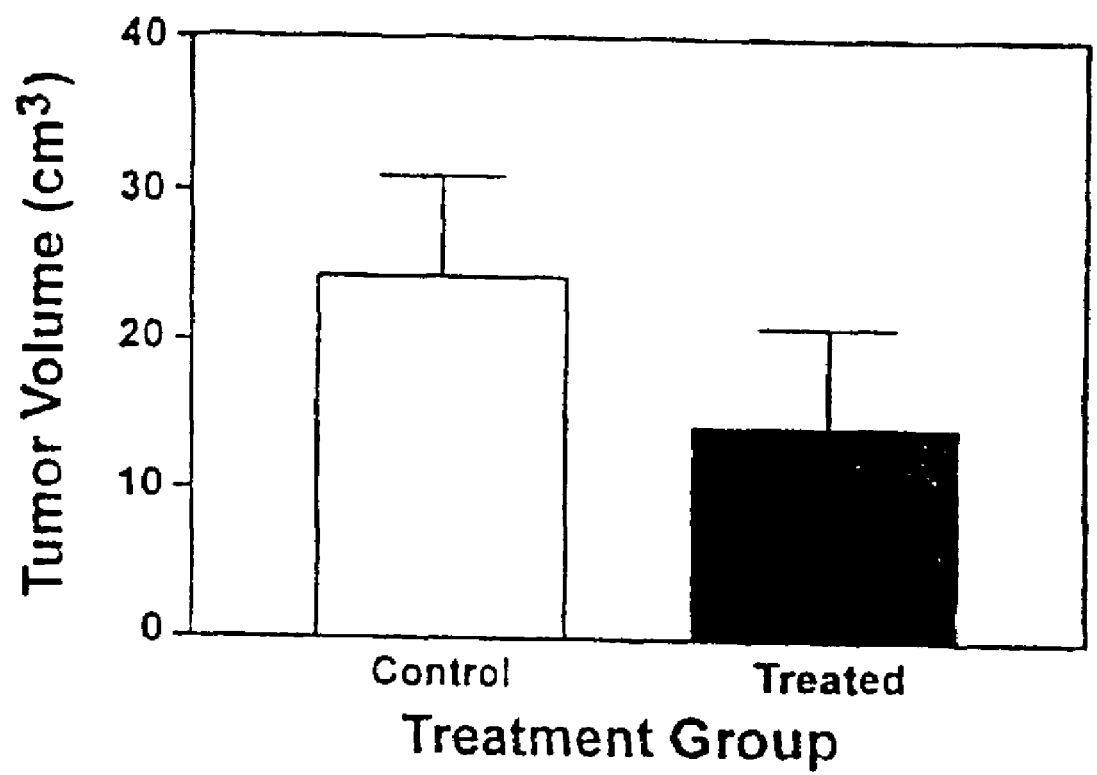
FIG. 10 depicts the effect of injection of the wild type human 238 base 3' UTR RNA (FIG. 3 and SEQ ID NO:3) on tumor growth in vivo in Example 1. The bars show mean tumor size and standard deviation on Day 30 following tumor injection, which was equal to 20 days after initial treatment. In the treated group, palpable primary tumors were injected with 10 micrograms of 238 base prohibitin 3' UTR RNA on Days 10 and 15 for a total of two doses. The control group was treated with isotonic saline carrier at the same time. The values are significantly different as determined by student's t-test (p≦0 01).

Direct injection of prohibitin 3' UTR transcripts, produced in vitro, into emerging palpable solid tumors at 9-12 days after passage significantly reduced both the growth rate and the final size of the tumors. The wild type, 238 base prohibitin 3' UTR RNA which demonstrated the ability to inhibit cell cycle progression in cell lines (FIGS. 6-8) was used. Inhibition of cell proliferation was observed when a primary tumor was treated with a single injection of 10 micrograms of RNA. In a series of ten treated animals (receiving a dose of 10 micrograms of RNA per injection and two injections) and ten control animals (receiving the saline carrier), the mean size (volume in cubic centimeters) of treated primary tumors was 42% (range 20-80%) smaller than control primary tumors at 30 days after passage (FIG. 10). All of the animals from the control group died (average lifespan=36±4 days), while four of the treated animals regressed to an apparently disease-free state and were healthy at 120 days past tumor injection. They had undergone complete regression of both the metastases and primary tumor by Day 45, indicating that a systemic anti-tumor activity was induced.

EXAMPLE 2

A 238 base RNA from the 3' end of the wild type prohibitin 3' UTR was examined for antiproliferative activity upon injection into rat mammary tumors in Wistar-Furth rats. Antiproliferative activity was observed with the prohibitin wild type RNA, while a control RNA had no effect on tumor growth.

Figure 11:
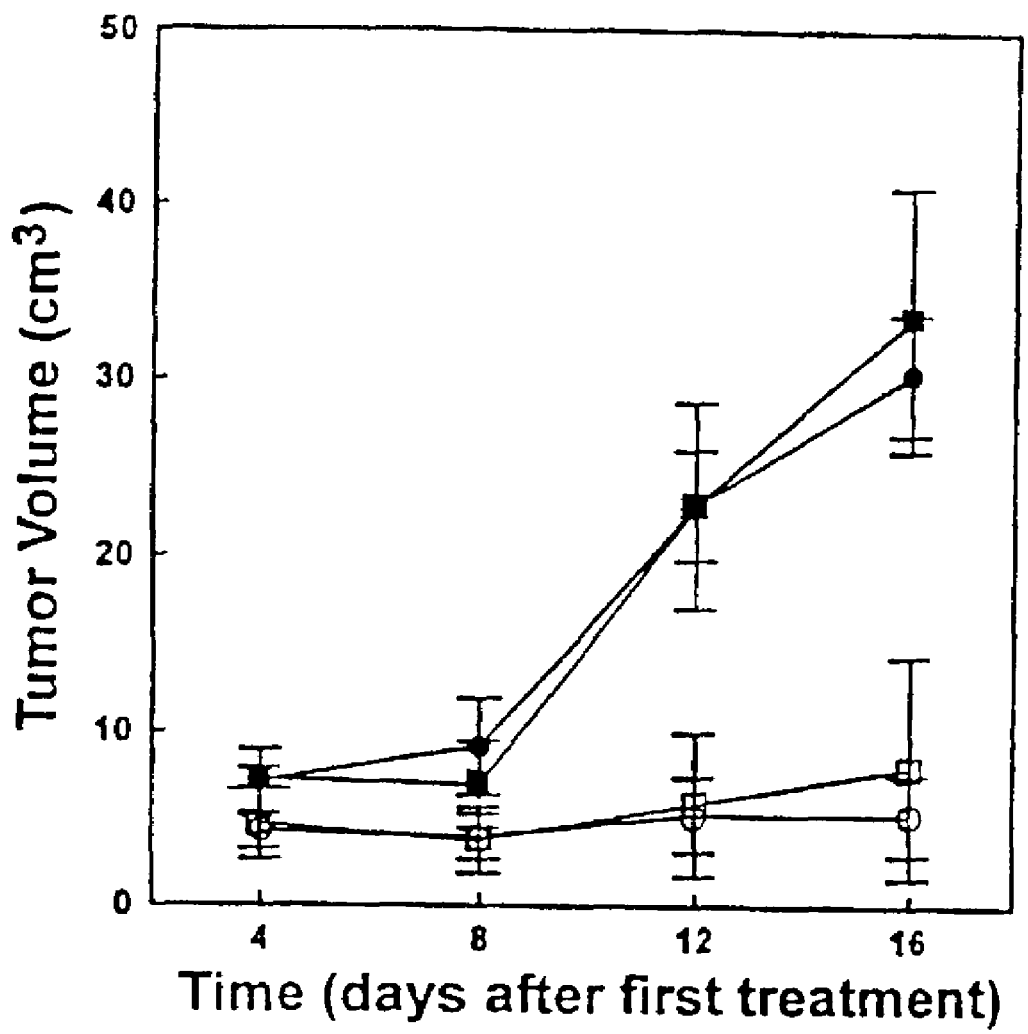
FIG. 11 depicts the effect of prohibitin 3' UTR RNA therapy on treatment groups from Example 2. Tumor volumes measured at four day intervals are shown for groups as closed circle=saline control, closed square=5' end of the 3' UTR control, open square=low dose wild type 3' end of the 3' UTR (10 micrograms of RNA per injection); and open circle=high dose wild type 3' end of the 3' UTR (20 micrograms of RNA per injection). The mean values with standard deviations are plotted.

Groups of five animals each were treated utilizing three injections into the primary tumor. There were two control groups, one receiving saline and another receiving RNA from the 5' end of the 3' UTR which was the same control used in cell proliferation assays (FIG. 6). The two treatment groups were low dose (10 micrograms in 100 microliters) and high dose (20 micrograms in 100 microliters) wild type RNA from the 3' end of the 3' UTR. By Day 16 after treatment, both groups of controls had tumors with a mean volume of about 30 cubic centimeters, while tumors in the low dose wild type treatment group were only 8 cubic centimeters and those of the high dose group were at 5 cubic centimeters (FIG. 11). Of the ten treated animals in this experiment, six animals were still alive and tumor free at 120 days after tumor injection as opposed to no animals in the control group. These results showed that both the dose and frequency of delivery altered the treatment efficacy.

EXAMPLE 3

Four treated animals from Example 1 and six treated animals from Example 2 underwent complete regression. In general, the animals that underwent regression had primary tumors that grew slowly, but they developed left and right axillary metastases. At approximately Day 15 following the initial treatment, the primary tumor ceased to grow, and the metastases also began to shrink. By Day 25, palpable metastases were no longer present, and the primary tumors had reduced in volume from a peak of about 20-30 cubic centimeters to only about 10 cubic centimeters. The primary tumors disappeared, and complete healing was observed between Day 35-45. The cured animals from Examples 1 and 2 remained disease free at 120 days after the initial tumor injection, while the average survival time of control animals was only 36 days. No spontaneous remission was observed in untreated animals or animals treated with control RNA.

This mode of regression, indicating that the prohibitin treatment triggers the development of an antitumor immune response, has now been tested by rechallenging 50 cured animals (120 days after initial challenge) with a fresh inoculation of the DMBA-4 tumor. Only 2 of the re-challenged animals developed tumors and the remaining 48 remained tumor free at 60 days after re-challenge showing that a long term immunity against the tumor was induced following successful prohibitin RNA therapy.

EXAMPLE 4

The antiproliferative activity of prohibitin RNA was assayed following the microinjection of RNA transcripts (Nuell, et al. 1991. Mol Cell Biol 11.1372-1381). Cells were synchronized in early G1 with lovastatin (provided by A. W. Alberts of Merck, Sharp and Dohme Research Pharmaceuticals, Rahway, N.J.) according to the method of Keyomarsi, et al 1991 *Cancer Res* 51 3602-3609. Synchronized cells (200-300 per experiment) were microinjected with an RNA transcript at a concentration of 1 mg/ml using an Eppendorf Model 5242 microinjector. Microinjected cells were allowed to move through the cell cycle in the presence of [$^3$H] thymidine, and inhibitory activity was calculated following autoradiography (Nuell, et al., *Mol Cell Biol* 11:1372-1381). These experiments show the antiproliferative activity is localized to a 238 base region at the 3' end of the 3' UTR (FIG. 6). Mutation in this region leads to loss of antiproliferative activity in both normal cells and breast cancer cells (FIGS. 7 & 8).

EXAMPLE 5

In this trial, sixteen Wistar-Furth rats were divided into two groups of eight. The control group of animals received an RNA 200 bases in length transcribed from the 5' end of the Xenopus elongation factor 1-α gene (Ambion Inc., Austin, Tex.). The treatment group received the 238 base RNA transcript from the 3' end of the prohibitin 3' UTR. Control and prohibitin RNAs were produced with 7-mG caps using the mMESSAGE mMACHINE transcription kit. Doses containing 20 micrograms of RNA each were delivered in DOTAP carrier by intratumoral injection from a syringe on days 12 and 17 after tumor inoculation. The capping of transcripts and delivery in DOTAP carrier produced rates of tumor regression similar to that seen in isotonic saline. However, a major improvement in survival percentage was observed. In this experiment by day 55, all of the control animals had died while seven of the treated animals were alive. Six of the prohibitin RNA treated animals (75%) were cured and remained tumor free at 120 days following tumor inoculation.

EXAMPLE 6

Patients with primary tumors and/or metastases can be treated with at least one prohibitin 3' UTR oligonucleotide of the present invention, preferably complexed with the carrier DOTAP. For patients with primary tumors, the oligonucleotide can be administered by direct injection into the primary tumor at from about 2 to about 120 micrograms per cubic centimeter tumor volume. For patients with metastases following surgical removal of the primary tumor, the oligonucleotide can be administered systemically at from about 0.5 to about 200 milligrams per kilogram body weight. An administration cycle can be from 1 to about 15 days. The administration cycle can be repeated multiple times. For patients with primary tumors and secondary metastases, the oligonucleotide can be administered by direct injection into the primary tumor at from about 2 to about 120 micrograms per cubic centimeter tumor volume followed by systemic administration at from about 0.5 to about 200 milligrams per kilogram body weight. Patient progress is monitored through methods known to medical community such as ultrasonic techniques to ascertain tumor size and status.

EXAMPLE 7

A patient diagnosed with breast cancer can be provided with oligonucleotide therapy according to the parameters provided in the above example prior to surgery. The administration of the oligonucleotides of the present invention can provide benefits of tumor regression and/or prevention of metastasis which could otherwise be prompted by the surgery as cells are disturbed in the mechanical process of tumor removal.

The invention claimed is:

1. An isolated and purified, single-stranded polynucleotide comprising at least 238 bases of the 3' untranslated region of a prohibitin gene defined by SEQ ID NO:1, wherein said polynucleotide lacks prohibitin sequences 5' to position 1566 of SEQ ID NO:1.

2. The isolated and purified, single-stranded polynucleotide of claim 1, wherein said polynucleotide is RNA.

3. The isolated and purified, single-stranded polynucleotide of claim 1, wherein said RNA is transcribed from said portion of said region.

4. The isolated and purified, single-stranded polynucleotide of claim 2, wherein said RNA is made synthetically according to a sequence coded for by said portion of said region.

5. The isolated and purified, single-stranded polynucleotide of claim 1 comprising a single stranded DNA having the sequence of said portion of said region.

6. The isolated and purified, single-stranded polynucleotide of claim 5, wherein said DNA is said portion of said region.

7. The isolated and purified, single-stranded polynucleotide of claim 5, wherein said DNA is made synthetically according to a sequence comprising said portion of said region.

8. A pharmaceutical preparation adapted for administration to obtain an antitumor effect, comprising a proliferation-inhibiting amount of a single-stranded polynucleotide comprising at least 238 bases of the 3' untranslated region of a prohibitin gene defined by SEQ ID NO:1, said preparation having proliferation-inhibiting activity in animals, wherein said polynucleotide lacks prohibitin sequences 5' to position 1566 of SEQ ID NO:1.

9. A method of inhibiting the proliferation of breast cancer cells in a subject comprising direct administration to said breast cancer cells of a proliferation-inhibiting amount of a polynucleotide comprising at least 238 bases of the 3' untranslated region of the prohibitin gene, whereby proliferation of said cancer cells in said subject is inhibited, wherein the prohibitin gene is defined by SEQ ID NO:1.

10. The method of claim 9, wherein said polynucleotide is selected from the group consisting of a ribonucleic acid transcribed from a portion of the 3' untranslated region of the prohibitin gene, a single-stranded deoxyribonucleic acid from the 3' untranslated region of the prohibitin gene, and mixtures thereof.

11. A method for preparing a pharmaceutical composition comprising formulating a proliferation-inhibiting amount of a single-stranded polynucleotide comprising at least 238 bases of a 3' untranslated region of a prohibitin gene, defined by SEQ ID NO:1, with isotonic saline, wherein said polynucleotide lacks prohibitin sequences 5' to position 1566 of SEQ ID NO:1.

12. A method for preparing a pharmaceutical composition comprising formulating a proliferation-inhibiting amount of single-stranded polynucleotide comprising at least 238 bases of a 3' untranslated region of a prohibitin gene, defined by SEQ ID NO:1, with DOTAP, wherein said polynucleotide lacks prohibitin sequences 5' to position 1566 of SEQ ID NO:1.

13. A vector comprising a polynucleotide comprising at least 238 bases of a 3' untranslated region of a prohibitin gene defined by SEQ ID NO:1, wherein said polynucleotide lacks prohibitin sequences 5' to position 1566 of SEQ ID NO:1.

14. A liposome for delivery to the patient comprising a single-stranded polynucleotide comprising at least 238 bases of a portion of the 3' untranslated region of a prohibitin gene defined by SEQ ID NO:1, wherein said polynucleotide lacks prohibitin sequences 5' to position 1566 of SEQ ID NO:1.

15. The method of claim 9, wherein said polynucleotide lacks prohibitin sequences 5' to position 867 of SEQ ID NO:1.

* * * * *

SEQUENCE LISTING

<160> NUMBER OF SEQ ID NOS: 7

<210> SEQ ID NO 1
<211> LENGTH: 1803
<212> TYPE: DNA
<213> ORGANISM: Homo sapiens

<400> SEQUENCE: 1

```
tgtggaggtc agagtggaag caggtgtgag agggtccagc agaaggaaac atggctgcca      60
aagtgtttga gtccattggc aagtttggcc tggccttagc tgttgcagga ggcgtggtga     120
actctgcctt atataatgtg gatgctgggc acagagctgt catctttgac cgattccgtg     180
gagtgcagga cattgtggta ggggaaggga ctcattttct catcccgtgg gtacagaaac     240
caattatctt tgactgccgt tctcgaccac gtaatgtgcc agtcatcact ggtagcaaag     300
atttacagaa tgtcaacatc acactgcgca tcctcttccg gcctgtcgcc agccagcttc     360
ctcgcatctt caccagcatc ggagaggact atgatgagcg tgtgctgccg tccatcacaa     420
ctgagatcct caagtcagtg gtggctcgct ttgatgctgg agaactaatc acccagagag     480
agctggtctc caggcaggtg agcgacgacc ttacagagcg agccgccacc tttgggctca     540
tcctggatga cgtgtccttg acacatctga ccttcgggaa ggagttcaca gaagcggtgg     600
aagccaaaca ggtggctcag caggaagcag agagggccag atttgtggtg gaaaaggctg     660
agcaacagaa aaaggcggcc atcatctctg ctgagggcga ctccaaggca gctgagctga     720
ttgccaactc actggccact gcaggggatg gcctgatcga gctgcgcaag ctggaagctg     780
cagaggacat cgcgtaccag ctctcacgct ctcggaacat cacctacctg ccagcggggc     840
agtccgtgct cctccagctg ccccagtgag ggcccaccct gcctgcacct ccgcgggctg     900
actgggccac agccccgatg attcttaaca cagccttcct tctgctccca ccccagaaat     960
cactgtgaaa tttcatgatt ggcttaaagt gaaggaaata aagtaaaat cacttcagat    1020 ctctaattag tctatcaaat gaaactcttt cattcttctc acatccatct acttttttat    1080
ccacctccct accaaaaatt gccaagtgcc tatgcaaacc agctttaggt cccaattcgg    1140
ggcctgctgg agttccggcc tgggcaccag catttggcag cacgcaggcg gggcagtatg    1200
tgatggactg gggagcacag gtgtctgcct agatccacgt gtggcctccg tcctgtcact    1260
gatggaaggt ttgcggatga gggcatgtgc ggctgaactg agaaggcagg cctccgtctt    1320
cccagcggtt cctgtgcaga tgctgctgaa gagaggtgcc ggggaggggc agagaggaag    1380
tggtctgtct gttaccataa gtctgattct ctttaactgt gtgaccagcg gaaacaggtg    1440
tgtgtgaact gggcacagat tgaagaatct gcccctgttg aggtgggtgg gcctgactgt    1500 tgcccccag ggtcctaaaa cttggatgga cttgtatagt gagagaggag gcctggaccg    1560
agatgtgagt cctgttgaag acttcctctc taccccccac cttggtccct ctcagatacc    1620
```

```
cagtggaatt ccaacttgaa ggattgcatc ctgctggggc tgaacatgcc tgccaaagac    1680
gtgtccgacc tacgttcctg gcccctcgt tcagagactg cccttctcac gggctctatg     1740
cctgcactgg gaaggaaaca aatgtgtata aactgctgtc aataaatgac acccagacct    1800
tcc                                                                   1803

<210> SEQ ID NO 2
<211> LENGTH: 852
<212> TYPE: DNA
<213> ORGANISM: Artificial Sequence
<220> FEATURE:
<223> OTHER INFORMATION: Description of Artificial Sequence: Primer

<400> SEQUENCE: 2
cccagaaatc actgtgaaat tcatgattg cttaaagtg aaggaaataa aggtaaaatc        60
acttcagatc tctaattagt ctatcaaatg aaactctttc attcttctca catccatcta    120
cttttttatc cacctcccta ccaaaaattg ccaagtgcct atgcaaacca gctttaggtc    180
ccaattcggg gcctgctgga gttccggcct gggcaccagc atttggcagc acgcaggcgg    240
ggcagtatgt gatggactgg ggagcacagg tgtctgccta gatccacgtg tggcctccgt    300
cctgtcactg atggaaggtt tgcggatgag ggcatgtgcg gctgaactga aaggcaggc     360 ctccgtcttc ccagcggttc ctgtgcagat gctgctgaag agaggtgccg gggaggggca    420
gagaggaagt ggtctgtctg ttaccataag tctgattctc tttaactgtg tgaccagcgg    480
aaacaggtgt gtgtgaactg ggcacagatt gaagaatctg cccctgttga ggtgggtggg    540
cctgactgtt gccccccagg gtcctaaaac ttggatggac ttgtatagtg agagaggagg    600
cctggaccga gatgtgagtc ctgttgaaga cttcctctct accccccacc ttggtccctc    660
tcagataccc agtggaattc caacttgaag gattgcatcc tgctggggct gaacatgcct    720
gccaaagacg tgtccgacct acgttcctgg cccctcgtt cagagactgc ccttctcacg     780
ggctctatgc ctgcactggg aaggaaacaa atgtgtataa actgctgtca ataaatgaca    840
cccagacctt cc                                                        852

<210> SEQ ID NO 3
<211> LENGTH: 260
<212> TYPE: DNA
<213> ORGANISM: Homo sapiens

<400> SEQUENCE: 3
gataatacga ctcactatag ggtgagtcct gttgaagact tcctctctac cccccaccctt    60 ggtccctctc agatacccag tggaattcca acttgaagga ttgcatcctg ctggggctga    120
acatgcctgc caaagacgtg tccgacctac gttcctggcc cctcgttca gagactgccc    180 ttctcacggg ctctatgcct gcactgggaa ggaaacaaat gtgtataaac tgctgtcaat    240
aaatgacacc cagaccttcc                                                260

<210> SEQ ID NO 4
<211> LENGTH: 239
<212> TYPE: DNA
<213> ORGANISM: Artificial Sequence
<220> FEATURE:
<223> OTHER INFORMATION: Description of Artificial Sequence: Primer

<400> SEQUENCE: 4
gtgagtcctg ttgaagactt cctctctacc ccccaccttg gtccctctca gatacccagt     60
```

-continued

```
ggaattccaa cttgaaggat tgcatcctgc tggggctgaa catgcctgcc aaagacgtgt    120
ccgacctacg ttcctggccc cctcgttcag agactgccct tctcacgggc tctatgcctg    180
cactgggaag gaaacaaatg tgtataaact gctgtcaata aatgacaccc agaccttcc    239
```

<210> SEQ ID NO 5
<211> LENGTH: 254
<212> TYPE: DNA
<213> ORGANISM: Rattus sp.

<400> SEQUENCE: 5

```
gtgagtcctg tggaagactt cctgtccacc ccccacattg gtcctctcaa atacccaatg     60
ggattccagc ttgaaggatt gcatcctgcc ggggctgagc acacctgcca aggacacgtg    120
cgcctgcctt cccgctccct ctcttcgaga ttgcccttcc ttcccaaggg ctgtgggcca    180
gagctccgaa ggaagcaatc aaggaaagaa aacacaatgt aagctgctgt caataaatga    240
cacccagacc ctca                                                      254
```

<210> SEQ ID NO 6
<211> LENGTH: 100
<212> TYPE: DNA
<213> ORGANISM: Artificial Sequence
<220> FEATURE:
<223> OTHER INFORMATION: Description of Artificial Sequence: Primer

<400> SEQUENCE: 6

```
gacacgtgcg cctgccttcc cgctccctct cttcgagatt gcccttcctt cccaagggct     60
gtgggccaga gctccgaagg aagcaatcaa ggaaagaaaa                          100
```

<210> SEQ ID NO 7
<211> LENGTH: 100
<212> TYPE: DNA
<213> ORGANISM: Artificial Sequence
<220> FEATURE:
<223> OTHER INFORMATION: Description of Artificial Sequence: Primer

<400> SEQUENCE: 7

```
gacacatgtg cctaccttcc cgcccctct ctccgagatt gcccttcctt cccaagggct      60
gtgggtcact gctccaaagg aagcaatcaa ggaaagaaaa                          100
```